United States Patent
Freytag et al.

(10) Patent No.: US 6,934,352 B2
(45) Date of Patent: Aug. 23, 2005

(54) METHOD AND APPARATUS AND COMPUTER PROGRAM PRODUCT FOR DETERMINING AN ABORT CRITERION DURING ACQUISITION OF 2D IMAGES OF A 3D SUBJECT

(75) Inventors: Rudolf Freytag, Bubenreuth (DE); Joachim Hornegger, Baiersdorf (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 10/641,177

(22) Filed: Aug. 14, 2003

(65) Prior Publication Data

US 2004/0066891 A1 Apr. 8, 2004

(30) Foreign Application Priority Data

Aug. 14, 2002 (DE) .......................................... 102 37 347

(51) Int. Cl.[7] ................................................. A61B 6/03
(52) U.S. Cl. ................................ 378/8; 378/4; 378/901
(58) Field of Search ............................ 378/4, 8, 15, 19, 378/901

(56) References Cited

U.S. PATENT DOCUMENTS

| | | |
|---|---|---|
| 5,612,985 A | 3/1997 | Toki et al. |
| 5,671,265 A | 9/1997 | Andress |
| 6,028,907 A | 2/2000 | Adler et al. |

OTHER PUBLICATIONS

"Image Reconstruction from Projections: The Fundamentals of Computerized Tomography," Herman (1980) pp. 90–107 and 180–205.
"Discrete Tomography: Foundations, Algorithms and Applications," Herman et al. (1999) pp. 3–33 and 285–296.
"Numerical Linear Algebra," Trefethen et al. (1997) pp. 25–31 and 89–96.
"Introductory Techniques for 3–D Computer Vision," Trucco et al., (1999) pp. 123–138.
"Visualisierung: Grundlagen un allgemeine Methoden," Schumann et al., (2000) pp. 251–306.
"Multiple View Geometry in Computer Vision," Hartley et al, (2000) pp. 441–482.
"Convergence of the Simultaneous Algebraic Reconstruction Technique (SART)" Jiang et al., Micro–CT Laboratory, Department of Radiology, University of Iowa (May 7, 2002).

*Primary Examiner*—David V Bruce
(74) *Attorney, Agent, or Firm*—Schiff Hardin LLP

(57) ABSTRACT

A 3-D subject is irradiated by an x-ray source at a number of source positions relative to the 3-D subject. A 2-D image of the irradiated subject is recorded by an x-ray detector at a number of corresponding detector positions relative to the subject. An evaluation unit, using the source and the detector positions, automatically determines whether a 3-D reconstruction of the subject is possible. As soon as this is the case, the abort criterion for recording images of the subject is fulfilled, so no further images or data are acquired.

46 Claims, 6 Drawing Sheets

METHOD AND APPARATUS AND COMPUTER PROGRAM PRODUCT FOR DETERMINING AN ABORT CRITERION DURING ACQUISITION OF 2D IMAGES OF A 3D SUBJECT

BACKGROUND OF THE INVENTION

1. Field of the Invention

The present invention concerns a method for determining an abort criterion during acquisition of two-dimensional images of a three-dimensional subject. The present invention also concerns a computer program product and an apparatus operating according to the method.

2. Description of the Prior Art

Methods of the above type are particularly necessary in x-ray imaging.

In each x-ray recording, the acquired two-dimensional (x-ray) detector signal (=the image) is used, among other things, to ascertain by means of the subject itself (in particular its absorption characteristics), the detector position relative to the subject and the source position relative to the subject. As used herein, the term "position" also can include the orientation of the x-ray detector or the x-ray source, if need be. Image I can therefore be written as:

$$I = P\, O.$$

wherein I is a vector that contains the entirety of a two-dimensional image, O is a vector that contains the volume elements of a three-dimensional subject, and P is an image matrix. In particular, they are ascertained relative to the subject by the positions of the x-ray source and the x-ray detector.

For a single projection, meaning a single image, the equation system above is generally not resolvable, i.e., the image matrix P is not invertible. The inversion is in fact ambiguous or undetermined. Given only one recording or only a few recordings, normally only a two-dimensional rendering of the projection of the subject is possible, but not a three-dimensional reconstruction of the subject.

With every further projection, further information is acquired about the subject. According to the Feldkamp algorithm, it is possible to calculate a three-dimensional reconstruction of the subject if x-ray source and x-ray detector rotate at least 180° around the subject on a common orbit. Along with the reconstruction of the three-dimensional subject per se, any two-dimensional projections as well as cross-sections are calculable and viewable. The Feldkamp algorithm is, for example, specified in "Image Reconstruction from Projections: The Fundamentals of Computerized Tomography", G. T. Herman, Academic Press, New York, 1980.

Rotation of the source and detector through at least 180° in a common orbit around the subject ensues in the fields of computed tomography and 3D-angiography. For example, in the field of computed tomography, it is further known in U.S. Pat. No. 6,028,907 and U.S. Pat. No. 5,612,985 to linearly move the subject perpendicular to the plane of the rotation simultaneously together with the rotation of the x-ray source and x-ray detector, such that, in effect, the x-ray source and the x-ray detector describe a helical path around the subject. In this case, a three-dimensional reconstruction is possible when the linear movement of the subject is not too large. A conversion into a circular motion around the subject must be possible—for example by interpolation.

As implemented above, the solution according to Feldkamp is to presume a predominantly circular motion of the x-ray source and the x-ray detector on a common orbit. The x-ray source and the x-ray detector thereby face one another with respect to the center of rotation. If the x-ray source and/or the x-ray detector effect something other than a circular motion around the axis of rotation, the reconstruction algorithm of Feldkamp is not applicable. A technique known as the ART-Method (ART=Algebraic Reconstruction Technique) is known from G. T. Herman, A. Kuba, Discrete Tomography: Foundations, Algorithms, and Applications, Springer Verlag, Telos, 1999. By means of this method, a reconstruction of a three-dimensional subject is possible in principle from a number of projections that can lie randomly. In particular, it is thus not essential in the acquisition of the images for the x-ray source and the x-ray detector to be rotated or otherwise moved on a common orbit around the subject.

SUMMARY OF THE INVENTION

An object of the present invention is to provide a determination method of the type initially described that allows a recognition as to whether a three-dimensional reconstruction of the subject is possible by means of the acquired images.

The object is thereby achieved in accordance with the invention in a method, a computer program product, and in x-ray examination apparatus, wherein a subject is transirradiated by an x-ray source at a number of source positions relative to the subject, and an image of the subject is recorded by an x-ray detector at a number of corresponding detector positions relative to the subject; and an evaluation unit automatically determines, using the source positions and the detector positions per se, whether a three-dimensional reconstruction of the subject is possible, dependent on an abort criterion that is fulfilled as soon as the three-dimensional reconstruction of the subject is possible.

The determination as to whether the three-dimensional reconstruction of the subject is possible preferably ensues in the following manner:

An equation system is determined that specifies functional dependencies of the images from volume data values. Each volume data value is accorded a position in space. The volume data values altogether describe the three-dimensional subject. The coefficients of the equation system are specified by the source positions and the detector positions and form a coefficient matrix with n columns and m rows. The evaluation unit, using the coefficient matrix, determines whether the three-dimensional reconstruction of the subject is possible.

The coefficient matrix is—by means of the known singular-value decomposition—viewable as a product of three matrices. The first matrix is an orthogonal quadratic matrix with m columns and m rows. The second matrix is a diagonal matrix with n columns and m rows. The third matrix is once again an orthogonal matrix with n columns and n rows. When the evaluation unit calculates the diagonal matrix, and with the diagonal matrix calculates whether the three-dimensional reconstruction of the subject is possible, the complexity of calculation is minimized.

The diagonal matrix contains diagonal coefficients. The evaluation unit calculates the largest diagonal coefficients according to magnitude and the number of diagonal coefficients whose ratio to the largest diagonal coefficients according to magnitude is larger than a condition number. The meaning of the condition number is, for example, specified in L. N. Trefethen, D. Bau: Numerical Linear Algebra, Siam Verlag, Philadelphia, 1997. The evaluation unit then compares these numbers with a variable number for the three-dimensional reconstruction of the subject. The variable number is the number of the volume data values to be determined. The complexity of calculation thereby can be minimized further. Alternatively, the condition number can be predetermined, or instead the evaluation unit can be preset by an operator of the evaluation unit.

It is possible to implement the evaluation method in advance purely by calculation. It is also possible to supply only the source and detector positions to the evaluation unit, but not the images themselves.

Preferably, at least the recorded images are supplied to the evaluation unit. Alternatively, the images thereby each can be supplied to the evaluation unit together with a source position and a corresponding detector position, or, can be supplied after the examination, assuming the three-dimensional reconstruction of the subject is possible. It is also possible to supply only the images to the evaluation unit and to automatically calculate the source positions and the corresponding detector positions by the evaluation unit using the supplied images.

The evaluation unit can discontinue the recording (acquisition) of images (or image data) as soon as the abort criterion is fulfilled, the complexity of the calculation to determine the three-dimensional reconstruction of the subject can be minimized. Furthermore, it is possible to automatically deactivate the x-ray source as well (if necessary) and thus minimize the x-ray exposure to the subject. The radiation exposure of the patient being examined is therefore no larger than absolutely necessary.

The evaluation unit also can discontinue the recording of images when a maximum number of images has been supplied to it, so an infinite number loop cycles due to unfavorable position defaults cannot occur. The maximum number can be predetermined by the evaluation unit itself. Alternatively, it can be predetermined by an entry into the evaluation unit by an operator of the evaluation unit.

It is possible for the evaluation unit to only serve as a buffer storage for the images supplied to it, and the reconstruction of the three-dimensional subject can ensue at another device. It is preferable, however, for the evaluation unit to determine the three-dimensional reconstruction of the subject, and in particular to do so immediately after the fulfillment of the abort criterion.

The evaluation unit preferably outputs a signal to the operator, which allows the operator to recognize whether the abort criterion has been fulfilled. This method is particularly meaningful when the position defaults ensue manually by the operator. The signal can be an optical signal, an acoustic signal, or another signal immediately perceptible by an operator.

Image reconstruction using any set of source and detector positions is possible by means of the inventive of determination method. In particular, the possibilities do not necessarily have to lie on an orbit or on a cylindrical surface.

It is possible that the evaluation unit does not directly control the x-ray source and the x-ray detector, but preferably they are positioned by the evaluation unit. The evaluation unit is thus preferably designed as evaluation and control unit.

When the positioning of the x-ray source and/or the x-ray detector ensues by means of an xyz-manipulator or multiple xyz-manipulators, the positions may be particularly flexibly predetermined.

DESCRIPTION OF THE PREFERRED EMBODIMENTS

Figure 1:
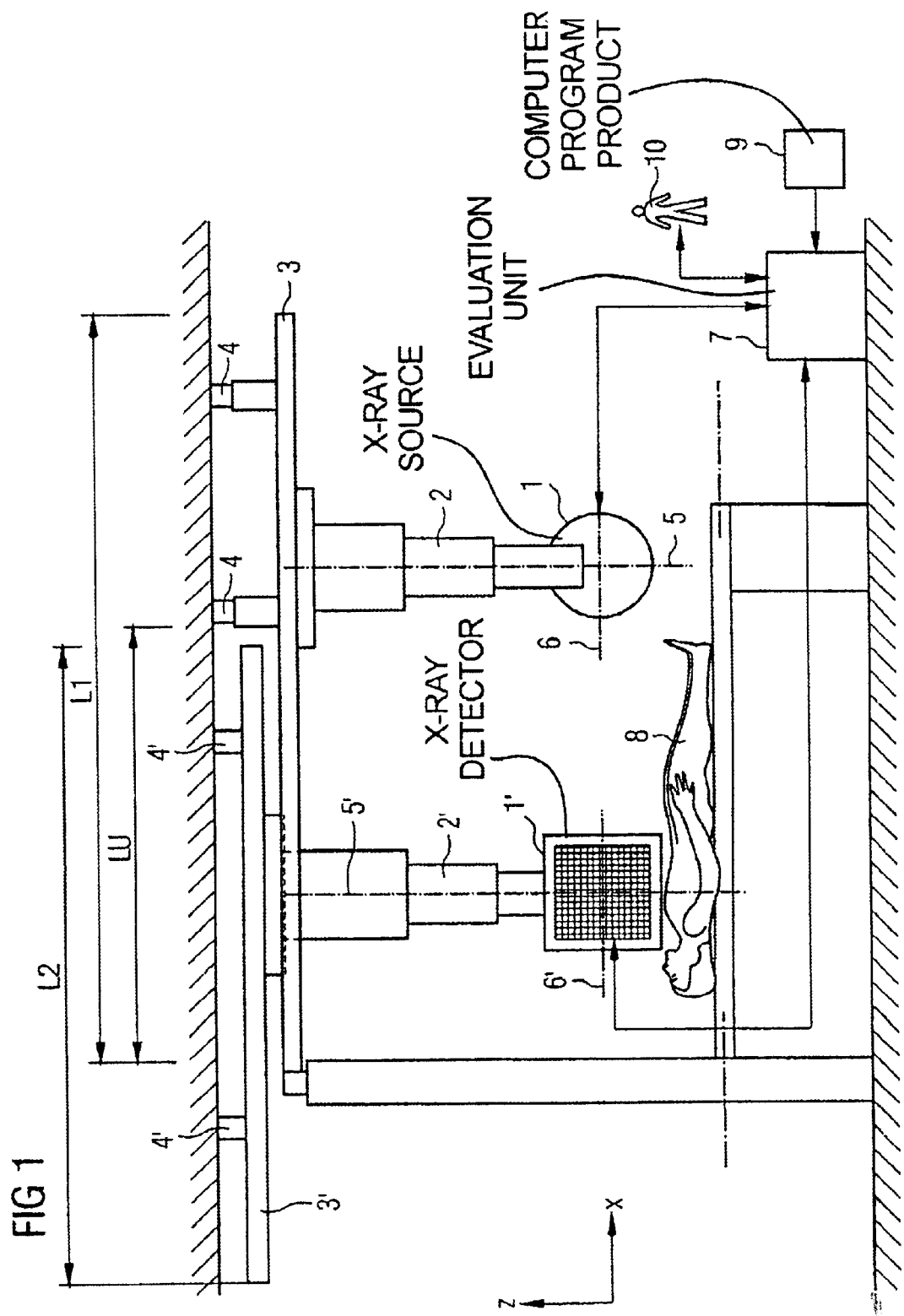
FIG. 1 is a side view of an x-ray installation constructed and operating in accordance with the invention.
Figure 2:
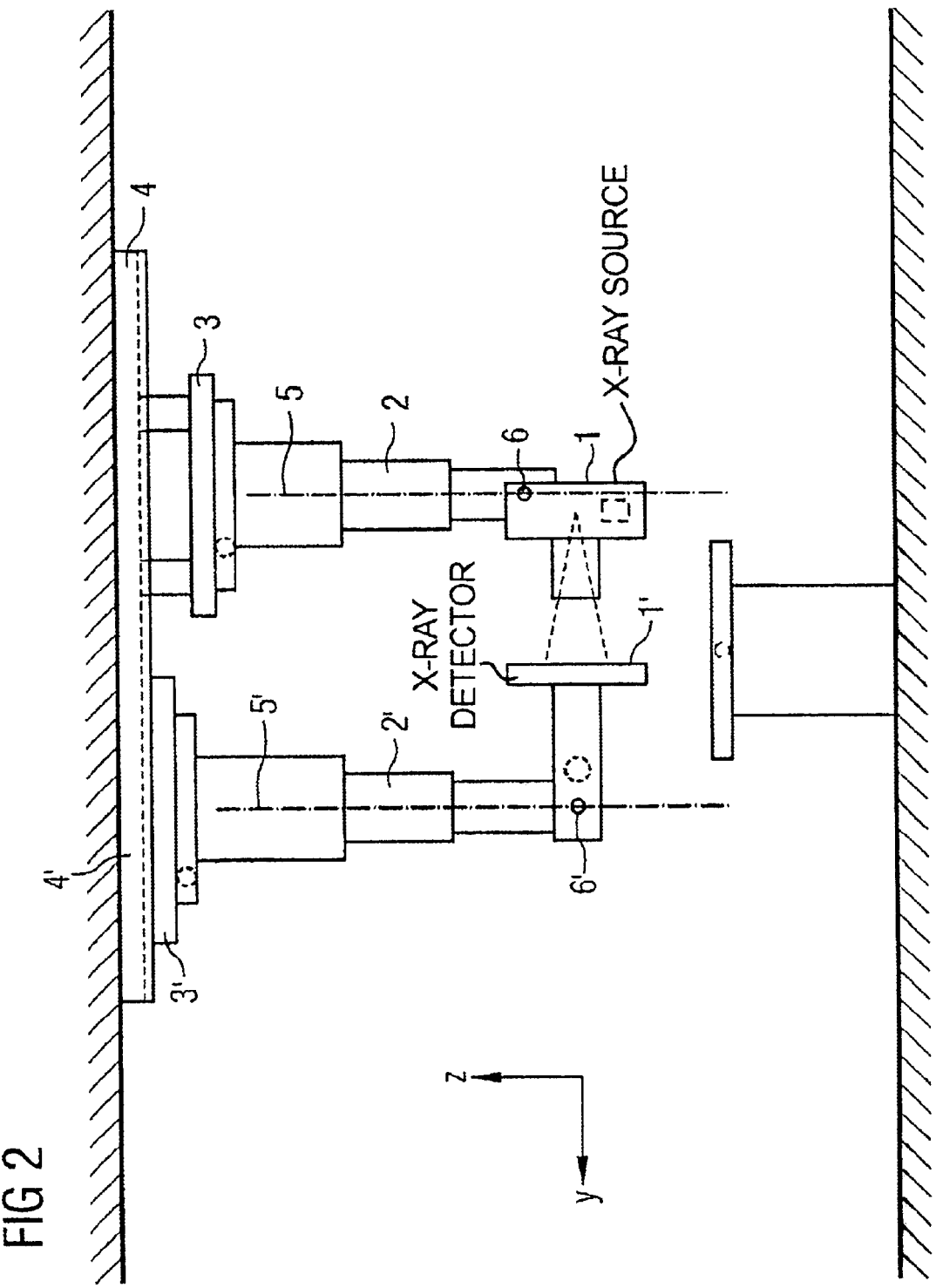
FIG. 2 is a front view of the x-ray installation of FIG. 1.

As shown in FIGS. 1 and 2, an x-ray installation has an x-ray source 1 and an x-ray detector 1'. The x-ray source 1 is arranged on a telescopic extendable column 2. By extending the column 2, the x-ray source 1 is moveable in a (vertical) direction z.

The column 2 is moveable in a (horizontal) direction x along a cross beam 3. The cross beam 3 is in turn movable along a main track 4 in a further (likewise horizontal) direction y. The x-ray source 1 also can be rotated around a middle axis 5 as well as around a rotational axis 6 perpendicular to the axis 5. The x-ray source 1 thus exhibits five degrees of freedom.

The directions x, y, and z form a right-hand Cartesian coordinate system. The column 2, the cross beam 3, and the main track 4 thus form an xyz-manipulator for the x-ray source 1.

The x-ray detector 1' is arranged likewise and exhibits the same degrees of freedom as the x-ray source 1. The components 2' through 6' correspond to those associated with x-ray source 1.

The x-ray source 1 and the x-ray detector 1' are connected in terms of information and control to a control and evaluation unit 1. For brevity, only the term "evaluation unit 7" will be used in the following. The x-ray source 1 and the x-ray detector 1' can be positioned at any point with any orientation relative to a three-dimensional subject 8 by means of the evaluation unit 7. Furthermore, the activation of the x-ray source 1 per se and the x-ray detector 1' per se is governed by the evaluation unit 7. The evaluation unit 7 thus controls the emission of x-rays by the x-ray source 1 and the x-ray detector 1' supplies received x-ray radiation to the evaluation unit 7 as two-dimensional images.

The evaluation unit 7 is programmed with a computer program product 9. Based on the programming of the evaluation unit 7 with the computer program product 9, [the evaluation unit 7] implements the following inventive determination method.

Figure 3:
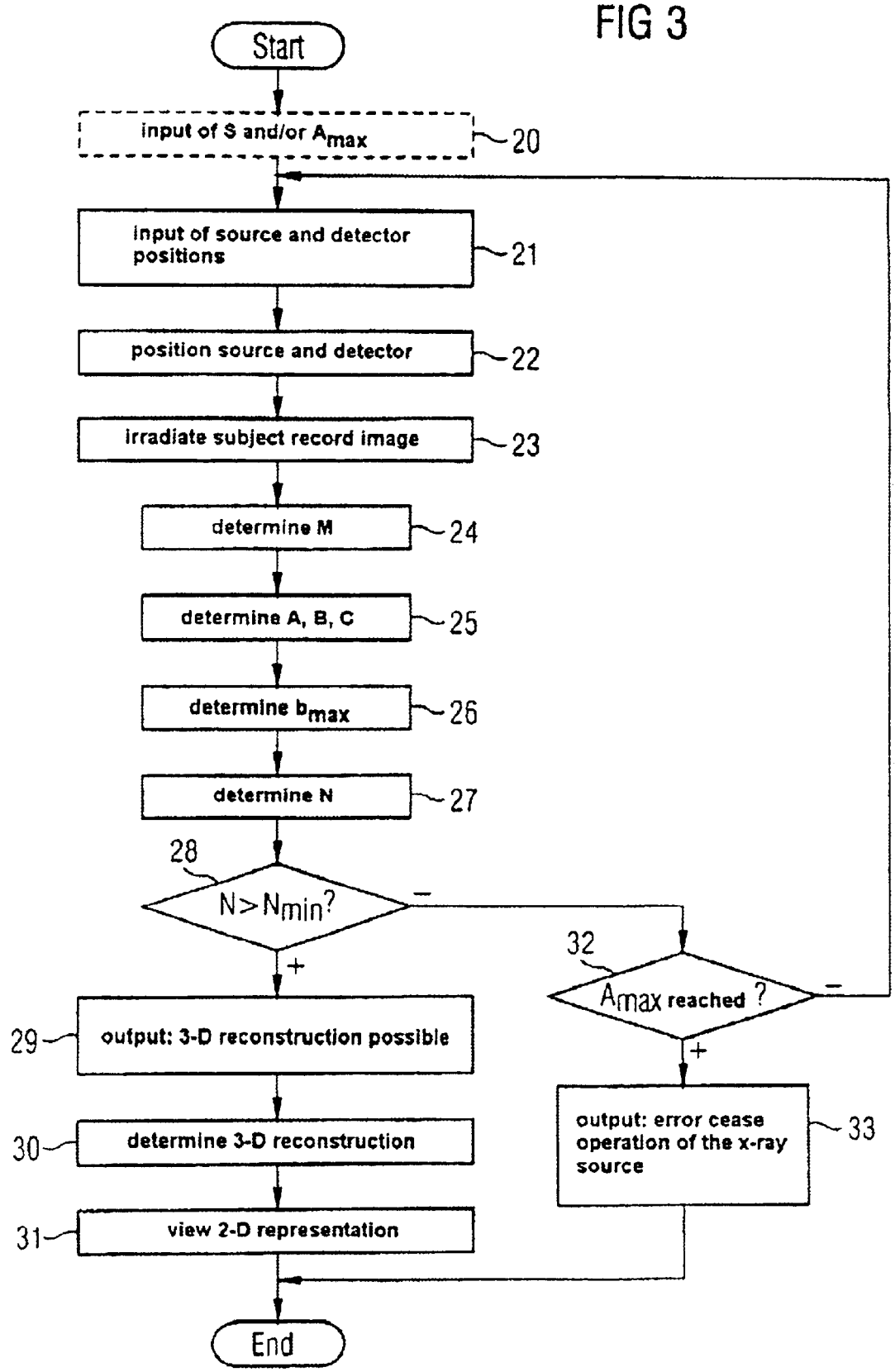
FIGS. 3 through 5 are flowcharts for explaining the inventive method.

As shown in FIG. 3, the evaluation unit 7 is next supplied by an operator 10 in step 21 with a source position of the x-ray source 1 relative to the subject 8, and a corresponding detector position of the x-ray detector 1' relative to the subject 8. The x-ray source 1 and the x-ray detector 1' are then positioned by the evaluation unit 7 in step 22, corresponding to the predetermined positions. The x-ray source 1 is then activated in step 23 by the evaluation unit 7, such that (at least for a short time) it emits x-ray radiation and thus irradiates the subject 8. The corresponding two-dimensional image is recorded immediately thereafter—likewise in step 23—by the x-ray detector 1' and is supplied to the evaluation unit 7.

A coefficient matrix M of an equation system $X=M \times Y$ is then determined by the evaluation unit 7 in step 24. X is a vector that contains all pixels of all viewed projections. Y is a vector of the volume data values. Each volume data value is a position assigned in space. In their entirety, the volume data values specify the three-dimensional subject 8. The coefficient matrix M has n columns and m rows. They specify the functional dependencies of the images on the volume data values.

To determine the equation system, it is necessary to know the projective image of three-dimensional space in the two-dimensional image plane of the x-ray detector 1'. The methods concerning this are generally known. For example, refer to E. Trucco, A. Verri, Introductory Techniques for 3-D Computer Vision, Prentice Hall, 1999. A linear equation is thus derived for each projection beam from the x-ray source 1 to the x-ray detector 1'. The entirety of the (two-dimensionally arranged) detector elements of the x-ray detector 1' thus supply the linear equation system. The coefficients of the equation system are thereby determined by the respective source and detector position. They form in their entirety the coefficient matrix M.

In order to be able to determine the volume data values, it is not sufficient to consider only the equation system that is derived from the a single projection. Likewise, a few small projections are normally insufficient. Included in the coefficient matrix M is not only the current projection, but also projections determined previously. The equation system thus grows with every further projection. The evaluation unit 7 is therefore able to automatically determine, using the source positions and the detector positions per se, whether a three-dimensional reconstruction of the subject 8 is possible. This ensues as follows:

Next, the coefficient matrix M is viewed in step 25 as the product of three matrices A, B, and C. The matrices A and C therein are quadratic, orthogonal matrices. Matrix A has m columns and m rows, matrix C has n columns and n rows. Matrix B is a diagonal matrix with n columns and m rows. It thus contains coefficients $b_{ij}$ that cannot be equal to zero only when the indices i and j have the same value. The coefficients $b_{ij}$, in which the indices i and j exhibit the same value, are designated as diagonal coefficients bi in the following.

The largest diagonal coefficients $b_{max}$ according to magnitude therefore can be determined in step 26. The number N, whose ratio to the largest diagonal coefficients $b_{max}$ according to magnitude is larger according to magnitude than a condition number S, can then be determined on diagonal coefficients bi in step 27. This number N is compared to a variable number $N_{min}$ in step 28. The variable number $N_{min}$ corresponds to the number of the volume data values to be determined. If the number N is larger or equal to the variable number $N_{min}$, an unambiguous determination of the volume data values is possible.

The evaluation unit 7 thus determines with the diagonal matrix B, and therefore indirectly with the coefficient matrix M, whether the three-dimensional reconstruction of the subject 8 is possible. Depending on the result of the examination in step 28, steps 29 through 31, or step 32, can therefore proceed.

A signal (preferably optical or acoustic) is output to the operator 10 by the evaluation unit 7 in step 29, such that the operator 10 can recognize that the three-dimensional reconstruction of the subject 8 is no longer possible, thus the abort criterion is fulfilled. Furthermore, the evaluation unit 7 discontinues more than just the recording of images. In particular, the x-ray source 1 is immediately deactivated. Furthermore, the three-dimensional reconstruction of the subject 8 is immediately subsequently determined in step 30. A random two-dimensional presentation of the determined volume data set can then ensue in step 31. The determination of such a presentation is specified, for example, in Schumann, Müller: Visualisierung, Springer Verlag, Heidelberg, 2000, Chapter 7.

If the variable number $N_{min}$ is not achieved in step 28, it is examined in step 32 whether the number of the images supplied to the evaluation unit 7 achieved a maximum number $A_{max}$. If this is the case, the detection of images in likewise discontinued in step 33. In particular, the evaluation unit 7 likewise ends the further operation of the x-ray source 1. Furthermore, a corresponding error message is output to the operator 10 in step 33.

When the maximum number Amax of images is still not achieved, the program jumps from step 32 to step 21, such that the operator 10 can predetermine a new source position and/or a new detector position.

In the embodiment specified above, the condition number S and the maximum number Amax are fixed. However, it is also possible, as indicated by dashed lines in FIG. 3, for the operator 10 of the evaluation unit 7 to preset these values S, Amax in step 20.

In the embodiment described above in connection with FIG. 3, the images are each supplied to the evaluation unit 7 with a source position and a corresponding detector position. However, it is also possible to supply only the images to the evaluation unit 7, without the corresponding source and detector positions. In this case, the evaluation unit 7 automatically determines the corresponding source and detector positions with the supplied images. A method to determine the corresponding source and detector positions is specified, for example, in R. Hartley, A. Zisserman: Multiple View Geometry in Computer Vision, published in Cambridge University Press, 200.

Furthermore, it is also possible to supply the images to the evaluation unit 7 only after testing whether the three-dimensional reconstruction of the subject 8 is possible. In this case, two different routines are executed by the evaluation unit 7, which are described below in connection with FIGS. 4 and 5. The same reference numbers used in FIGS. 3 and 4 indicate the same steps as in FIG. 3.

Figure 4:
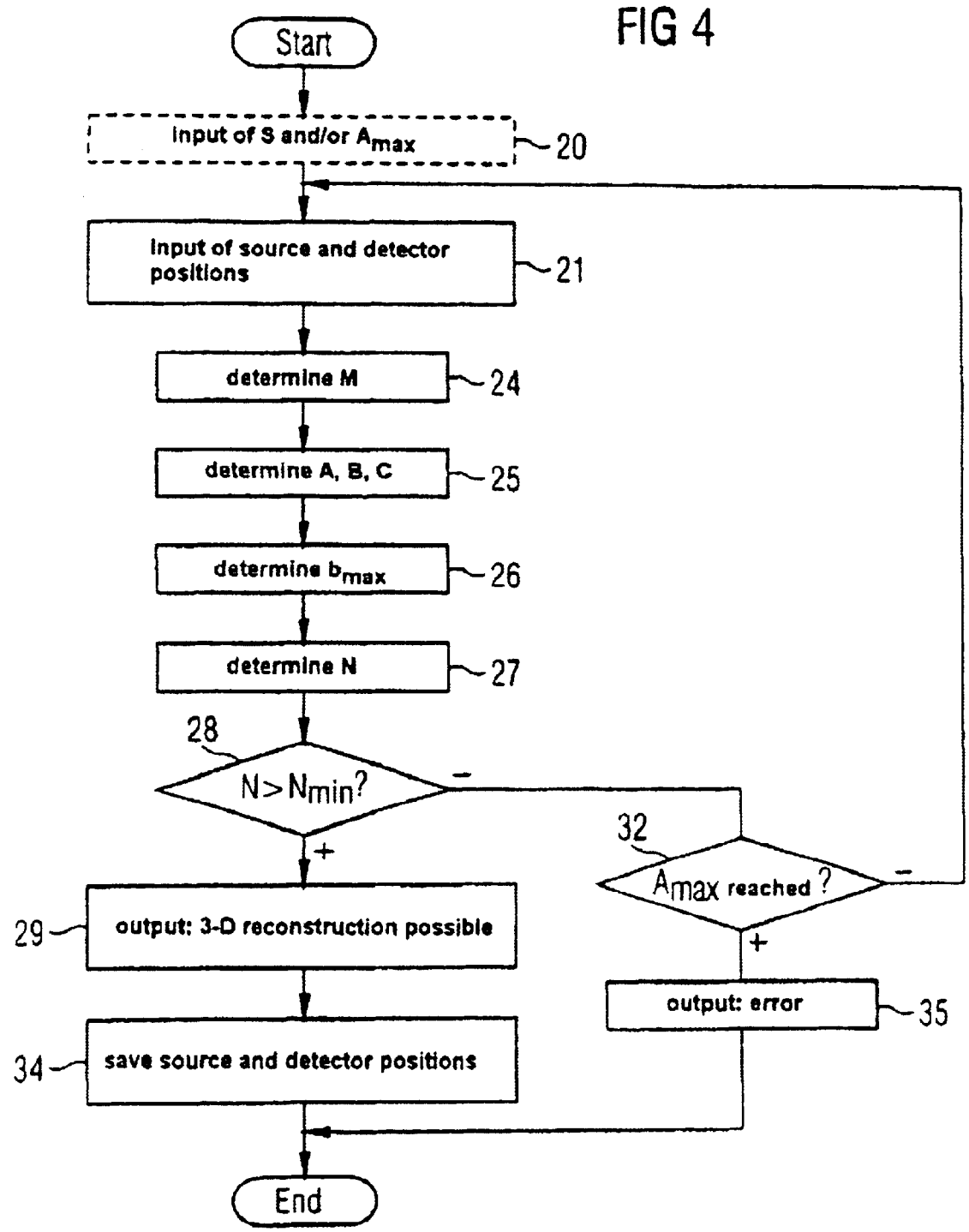

The routine according to FIG. 4 primarily includes the determination of a group of source and detector positions, by means of which a three-dimensional reconstruction of the subject 8 is later possible. The only steps not already explained in connection with FIG. 3 are steps 34 and 35. A group of determined source and detector positions is stored in step 34. An error message is output in step 35, but the operation of the x-ray source 1 is not simultaneously ended, because it would not have been operated in the first place.

Figure 5:
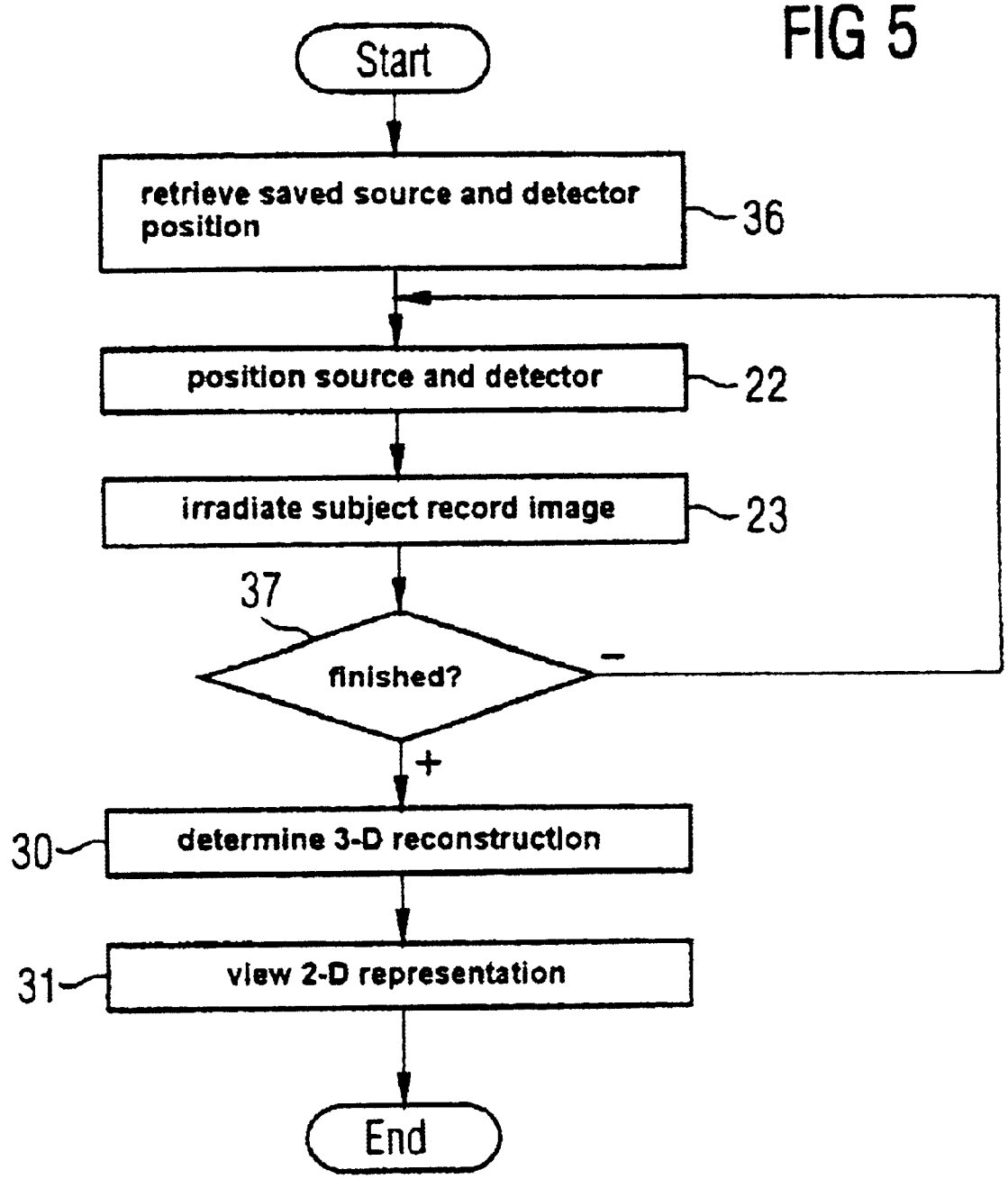

The only steps in FIG. 5 that are not already explained in FIG. 3 are steps 36 and 37. In step 36, the group of source and detector positions that were stored in step 34 (FIG. 4) are retrieved. In step 37, it is only tested whether all of the positions retrieved in step 36 were already occupied.

The source and detector positions, in principle, can be randomly chosen. In particular, they need not lie on an orbit nor on a cylindrical surface. For example, such position results are presented in FIGS. 6 through 9.

Figure 6:
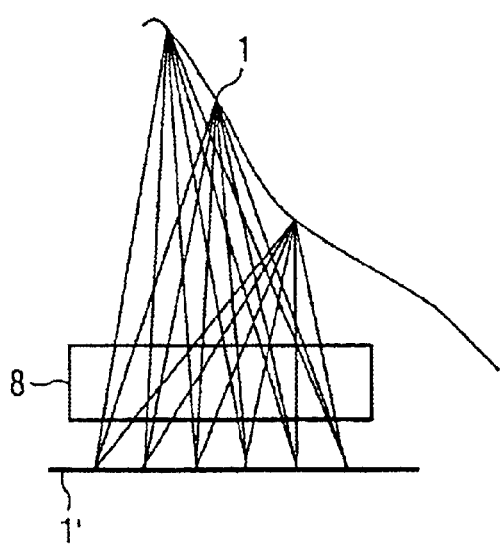
FIGS. 6 through 9 illustrate exemplary source and detector positions that can occur in the operation of the inventive x-ray installation.
Figure 7:
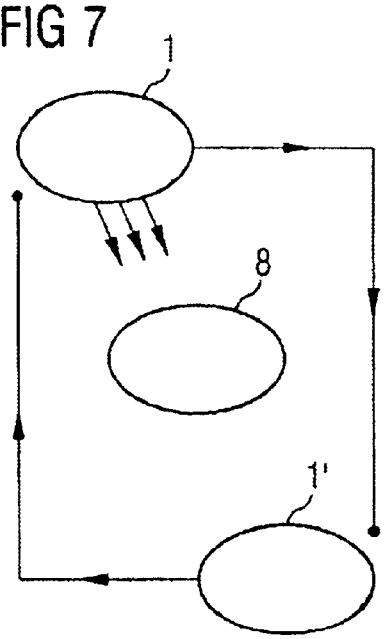
Figure 8:
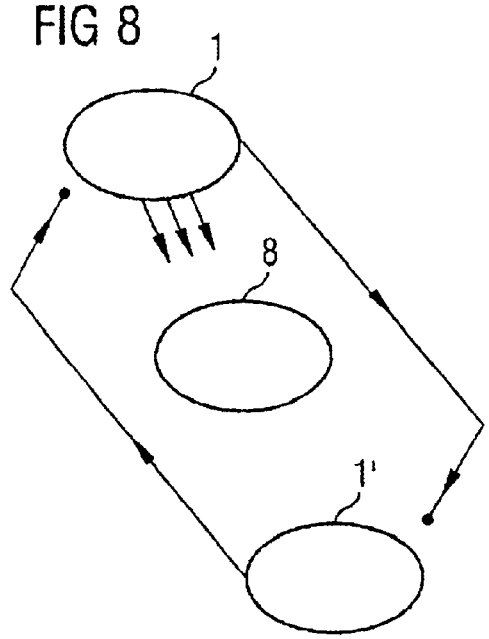
Figure 9:
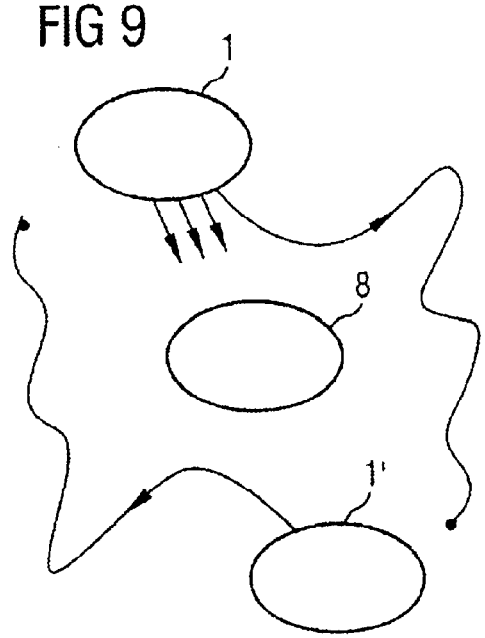

For example, according to FIG. 6, only the x-ray source 1 moves to different positions, whereas the x-ray detector 1' remains stationary. According to FIGS. 7 through 9, the x-ray source 1 and the x-ray detector 1' move symmetrically, but not in an orbit around a common rotational axis.

The presentations according to FIGS. 6 through 9 are only examples, among other possibilities. Other random movement paths are also possible, when a three-dimensional reconstruction of the subject 8 is only possible afterwards. For example, the x-ray source 1 and the x-ray detector 1' could start from the outer edges of octants of a sphere lying opposite to one another. Likewise, for example, the x-ray source 1 and the x-ray detector 1' could be held in their original positions, and the subject 8 rotated and/or moved. It is only important that the three-dimensional reconstruction of the subject 8 is possible on the grounds of the determined two-dimensional images.

The inventive method of determination is preferably employed in the field of medicine, however, it is not limited to the field of medicine. In particular, it could also be employed for material examination baggage inspection at airports. In the latter case, it is possible, for example, to mount the x-ray source 1 and the x-ray detector 1' as stationary and to move the subject to be examined relative to them.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining an abort criterion during acquisition of a plurality of two-dimensional images of a three-dimensional subject, comprising the steps of:

irradiating a subject with x-rays from an x-ray source at a plurality of positions of said x-ray source relative to the subject and, for each position of said x-ray source, acquiring two-dimensional image data of the subject corresponding to attenuation of the x-rays by the subject, with a radiation detector at a plurality of positions of the radiation detector respectively correlated to the position of the x-ray source;

using the respective positions of the x-ray source and the radiation detector, automatically electronically determining, as said two-dimensional image data are acquired for the respective positions, whether a three-dimensional image reconstruction of the subject is possible from an accumulated amount of said two-dimensional image data; and electronically determining an abort criterion, which ceases irradiation of the subject, to be fulfilled as soon as said three-dimensional image reconstruction of the subject is possible.

2. A method as claimed in claim 1 wherein the step of automatically electronically determining whether a three-dimensional of the subject is possible from an accumulated amount of said two-dimensional image data comprises:

determining an equation system that specifies functional dependencies of the 2D image data on volume data values for said three-dimensional image reconstruction;

according each volume data value a position in space so that a totality of said volume data values defines a three-dimensional subject;

electronically ascertaining coefficients for said equation system using the respective positions of said x-ray source and said radiation detector;

electronically entering said coefficients into a coefficient matrix with n columns and m rows; and electronically determining from said coefficient matrix whether said three-dimensional image reconstruction of the subject is possible.

3. A method as claimed in claim 2 wherein the step of using said coefficient matrix to determine whether said three-dimensional image reconstruction of the subject is possible comprises:

electronically analyzing said coefficient matrix as a product of three matrices, with a first of said three matrices being an orthogonal quadratic matrix with n columns and m rows, and wherein a second of said three matrices is a diagonal matrix with n columns and m rows, and wherein a third of said three matrices is an orthogonal quadratic matrix with n columns and m rows; and electronically using said diagonal matrix to determine whether said three-dimensional image reconstruction of the subject is possible.

4. A method as claimed in claim 3 wherein said diagonal matrix is comprised of diagonal coefficients, and wherein the step of electronically using said diagonal matrix to determine whether said three-dimensional image reconstruction of the subject is possible comprises:

determining a largest of said diagonal coefficients as to magnitude;

determining a number of said diagonal coefficients having respective magnitudes for which a ratio thereof relative to the magnitude of said largest diagonal coefficients exceeds a conditional number; and comparing said number of diagonal coefficients to a variable number for said three-dimensional image reconstruction of the subject.

5. A method as claimed in claim 4 comprising employing a predetermined number as said conditional number.

6. A method as claimed in claim 4 comprising allowing manual selection of said conditional number by a user.

7. A method as claimed in claim 1 comprising automatically electronically determining whether said three-dimensional image reconstruction of the subject is possible in an evaluation unit, and supplying said evaluation unit with said two-dimensional image data.

8. A method as claimed in claim 7 comprising supplying signals representing the respective positions of said x-ray source and said radiation detector to said evaluation unit.

9. A method as claimed in claim 8 comprising supplying said two-dimensional image data to said evaluation unit only after testing in said evaluation unit whether said three-dimensional image reconstruction of the subject is possible.

10. A method as claimed in claim 8 comprising supplying said two-dimensional image data to said evaluation unit together with information designating the respective positions of the x-ray source and the radiation detector.

11. A method as claimed in claim 7 comprising supplying said evaluation unit only with said two-dimensional image and in said evaluation unit, automatically electronically determining the respective positions of the x-ray source and the radiation detector from the two-dimensional image data.

12. A method as claimed in claim 7 comprising automatically discontinuing acquisition of said two-dimensional image data by said radiation detector when said abort criterion is fulfilled.

13. A method as claimed in claim 1 comprising discontinuing acquisition of said two-dimensional image data by said radiation detector when a maximum amount of two-dimensional image data have been acquired.

14. A method as claimed in claim 13 comprising employing a predetermined maximum amount as said maximum amount of two-dimensional image data.

15. A method as claimed in claim 13 comprising allowing selection by a user of said maximum amount of two-dimensional image data.

16. A method as claimed in claim 1 comprising determining whether said three-dimensional image reconstruction of the subject is possible in an evaluation unit, and reconstructing a three-dimensional image of the subject in the evaluation unit.

17. A method as claimed in claim 16 comprising reconstructing said three-dimensional image of the subject in said evaluation unit immediately after said abort criterion is fulfilled.

18. A method as claimed in claim 1 comprising electronically generating a humanly perceptible signal when said abort criterion is fulfilled.

19. A method as claimed in claim 1 comprising irradiating the subject along a path followed by the x-ray source and the radiation detector wherein the respective positions of the x-ray source and the radiation detector do not lie on an orbit around the examination subject nor on a cylindrical surface around said examination subject.

20. A method as claimed in claim 1 comprising determining whether said three-dimensional image reconstruction of the subject is possible in an evaluation unit, and controlling the respective positions of the x-ray source and the radiation detector with said evaluation unit.

21. A method as claimed in claim 20 comprising controlling the respective positions of the x-ray source and the radiation detector by at least one xyz manipulator operated by said evaluation unit and to which said x-ray source and said radiation detector are connected.

22. A computer program product for determining an abort criterion during acquisition of a plurality of two-dimensional images of a three-dimensional subject in a computed tomography system having an x-ray source which irradiates a subject with x-rays at a plurality of positions of said x-ray source relative to the subject and a two-dimensional radiation detector that, for each position of said x-ray source, acquires two-dimensional image data of the subject, corresponding to attenuation of the x-rays by the subject, at a plurality of positions of the radiation detector respectively correlated with the positions of the x-ray source, and having an evaluation unit into which the computer program product is loaded for programming the evaluation unit to:

use the respective positions of the x-ray source and the radiation detector to automatically electronically determine, as said two-dimensional image data are acquired for respective positions, whether a three-dimensional image reconstruction of the subject is possible from an accumulated amount of said two-dimensional image data; and determine an abort criterion, which ceases irradiation of the subject, as being fulfilled as soon as said three-dimensional image reconstruction of the subject is possible.

23. A computer program product as claimed in claim 22 which programs the evaluation unit to automatically electronically determine whether a three-dimensional of the subject is possible from an accumulated amount of said two-dimensional image data by:

determining an equation system that specifies functional dependencies of the 2D image data on volume data values for said three-dimensional image reconstruction;

according each volume data value a position in space so that a totality of said volume data values defines a three-dimensional subject;

ascertaining coefficients for said equation system using the respective positions of said x-ray source and said radiation detector;

entering said coefficients into a coefficient matrix with n columns and m rows; and determining from said coefficient matrix whether said three-dimensional image reconstruction of the subject is possible.

24. A computer program product as claimed in claim 23 which programs the evaluation unit to use said coefficient matrix to determine whether said three-dimensional image reconstruction of the subject is possible by:

analyzing said coefficient matrix as a product of three matrices, with a first of said three matrices being an orthogonal quadratic matrix with n columns and m rows, and wherein a second of said three matrices is a diagonal matrix with n columns and m rows, and wherein a third of said three matrices is an orthogonal quadratic matrix with n columns and m rows; and using said diagonal matrix to determine whether said three-dimensional image reconstruction of the subject is possible.

25. A computer program product as claimed in claim 24 wherein said diagonal matrix is comprises of diagonal coefficients, and which programs the evaluation unit to use said diagonal matrix to determine whether said three-dimensional image reconstruction of the subject is possible by:

determining a largest of said diagonal coefficients as to magnitude;

determining a number of said diagonal coefficients having respective magnitudes for which a ratio thereof relative to the magnitude of said largest diagonal coefficients exceeds a conditional number; and comparing said number of diagonal coefficients to a variable number for said three-dimensional image reconstruction of the subject.

26. A computer program product as claimed in claim 25 that includes a predetermined number as said conditional number.

27. A computer program product as claimed in claim 25 that allows allowing manual selection of said conditional number by a user into the evaluation unit.

28. An x-ray imaging apparatus comprising of:

an x-ray source for irradiating a subject with x-rays at a plurality of positions of said x-ray source relative to the subject and a two-dimensional radiation detector for, for each position of said x-ray source, acquiring two-dimensional image data of the subject, corresponding to attenuation of the x-rays by the subject, at a plurality of positions of the radiation detector respectively correlated with the positions of the x-ray source; and an evaluation unit that uses the respective positions of the x-ray source and the radiation detector to automatically, electronically determine, as said two-dimensional image data are acquired for respective positions, whether a three-dimensional image reconstruction of the subject is possible from an accumulated amount of said two-dimensional image data, and that determines an abort criterion, which ceases irradiation of the subject, as being fulfilled as soon as said three-dimensional image reconstruction of the subject is possible.

29. An x-ray imaging apparatus as claimed in claim 28 wherein the evaluation unit automatically electronically determines whether a three-dimensional of the subject is possible from an accumulated amount of said two-dimensional image data by determining an equation system that specifies functional dependencies of the 2D image data on volume data values for said three-dimensional image reconstruction, according each volume data value a position in space so that a totality of said volume data values defines a three-dimensional subject, ascertaining coefficients for said equation system using the respective positions of said x-ray source and said radiation detector, entering said coefficients into a coefficient matrix with n columns and m rows, and determining from said coefficient matrix whether said three-dimensional image reconstruction of the subject is possible.

30. An x-ray imaging apparatus as claimed in claim 29 wherein the evaluation unit uses said coefficient matrix to determine whether said three-dimensional image reconstruction of the subject is possible by analyzing said coefficient matrix as a product of three matrices, with a first of said three matrices being an orthogonal quadratic matrix with n columns and m rows, and wherein a second of said three matrices is a diagonal matrix with n columns and m rows, and wherein a third of said three matrices is an orthogonal quadratic matrix with n columns and m rows, and using said diagonal matrix to determine whether said three-dimensional image reconstruction of the subject is possible.

31. An x-ray imaging apparatus as claimed in claim 30 wherein said diagonal matrix is comprises of diagonal coefficients, and wherein the evaluation unit uses said diagonal matrix to determine whether said three-dimensional image reconstruction of the subject is possible by determining a largest of said diagonal coefficients as to magnitude, determining a number of said diagonal coefficients having respective magnitudes for which a ratio thereof relative to the magnitude of said largest diagonal coefficients exceeds a conditional number, and comparing said number of diagonal coefficients to a variable number for said three-dimensional image reconstruction of the subject.

32. An x-ray imaging apparatus as claimed in claim 31 wherein the evaluation unit employs a predetermined number as said conditional number.

33. An x-ray imaging apparatus as claimed in claim 31 comprising an input unit, connected to the evaluation unit, allowing manual selection of said conditional number by a user.

34. An x-ray imaging apparatus as claimed in claim 28 wherein said radiation detector supplies said two-dimensional image data to said evaluation unit only after testing in said evaluation unit whether said three-dimensional image reconstruction of the subject is possible.

35. An x-ray imaging apparatus as claimed in claim 28 wherein said radiation detector supplies said two-dimensional image data to said evaluation unit together with information designating the respective positions of the x-ray source and the radiation detector and wherein the x-ray source supplies information to the evaluation unit designating the respective positions of the x-ray source.

36. An x-ray imaging apparatus as claimed in claim 28 wherein the radiation detector supplies said evaluation unit only with said two-dimensional image, and wherein said evaluation unit, automatically electronically determines the respective positions of the x-ray source and the radiation detector from the two-dimensional image data.

37. An x-ray imaging apparatus as claimed in claim 28 wherein the evaluation unit automatically discontinues acquisition of said two-dimensional image data by said radiation detector when said abort criterion is fulfilled.

38. An x-ray imaging apparatus as claimed in claim 28 wherein the evaluation unit discontinues acquisition of said two-dimensional image data by said radiation detector when a maximum amount of two-dimensional image data have been acquired.

39. An x-ray imaging apparatus as claimed in claim 38 wherein the evaluation unit employs a predetermined maximum amount as said maximum amount of two-dimensional image data.

40. An x-ray imaging apparatus as claimed in claim 38 comprising an input unit, connected to the evaluation unit, allowing selection by a user of said maximum amount of two-dimensional image data.

41. An x-ray imaging apparatus as claimed in claim 28 wherein the evaluation unit reconstructs the three-dimensional image of the subject from the accumulated amount of two-dimensional data.

42. An x-ray imaging apparatus as claimed in claim 41 wherein the evaluation unit reconstructs said three-dimensional image of the subject immediately after said abort criterion is fulfilled.

43. An x-ray imaging apparatus as claimed in claim 28 wherein the evaluation unit generates a humanly perceptible signal when said abort criterion is fulfilled.

44. An x-ray imaging apparatus as claimed in claim 28 comprising a mounting arrangement for the x-ray source and the radiation detector that moves the x-ray source and the radiation detector in a path while the subject is being irradiated wherein the respective positions of the x-ray source and the radiation detector do not lie on an orbit around the examination subject nor on a cylindrical surface around said examination subject.

45. An x-ray imaging apparatus as claimed in claim 28 wherein the evaluation unit operated the mounting arrangement to control the respective positions of the x-ray source and the radiation detector.

46. An x-ray imaging apparatus as claimed in claim 28 wherein said mounting arrangement is at least one xyz manipulator operated by said evaluation unit.

* * * * *